US008634931B2

(12) United States Patent
Min et al.

(10) Patent No.: US 8,634,931 B2
(45) Date of Patent: Jan. 21, 2014

(54) MRI COMPATIBLE IMPLANTABLE MEDICAL LEAD AND METHOD OF MAKING SAME

(75) Inventors: Xiaoyi Min, Thousand Oaks, CA (US); J. Christopher Moulder, Lake Balboa, CA (US); Yong D. Zhao, Simi Valley, CA (US); Virote Indravudh, Santa Clarita, CA (US); Ingmar Viohl, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 1195 days.

(21) Appl. No.: 12/262,047

(22) Filed: Oct. 30, 2008

(65) Prior Publication Data

US 2010/0114276 A1 May 6, 2010

(51) Int. Cl.
*A61N 1/00* (2006.01)

(52) U.S. Cl.
USPC ............ 607/115; 607/116; 607/119; 607/122

(58) Field of Classification Search
USPC .................................. 607/115, 116, 119, 122
See application file for complete search history.

(56) References Cited

U.S. PATENT DOCUMENTS

2005/0113873 A1* 5/2005 Weiner et al. ...................... 607/2
2006/0252314 A1* 11/2006 Atalar et al. ................... 439/876
2007/0112398 A1 5/2007 Stevenson et al.
2008/0132986 A1 6/2008 Gray et al.
2008/0132987 A1 6/2008 Westlund et al.
2008/0161886 A1 7/2008 Stevenson et al.
2008/0243218 A1 10/2008 Bottomley et al.
2008/0262584 A1 10/2008 Bottomley et al.

FOREIGN PATENT DOCUMENTS

WO 2007102893 A2 9/2007
WO 2007102893 A3 9/2007

* cited by examiner

*Primary Examiner* — Michael Kahelin
*Assistant Examiner* — Mallika D Fairchild

(57) ABSTRACT

An implantable medical lead is disclosed herein. In one embodiment, the lead includes a body and an electrical pathway. The body may include a distal portion with an electrode and a proximal portion with a lead connector end. The electrical pathway may extend between the electrode and lead connector end and include a coiled inductor including a first portion and a second portion at least partially magnetically decoupled from the first portion. The first portion may include a first configuration having a first SRF. The second portion may include a second configuration different from the first configuration. The second configuration may have a second SRF different from the first SRF. For example, the first SRF may be near 64 MHz and the second SRF may be near 128 MHz.

20 Claims, 10 Drawing Sheets

MRI COMPATIBLE IMPLANTABLE MEDICAL LEAD AND METHOD OF MAKING SAME

CROSS-REFERENCE TO RELATED APPLICATIONS

This application is related to copending U.S. patent application Ser. No. 12/262,083, filed concurrently herewith, titled "MRI Compatible Implantable Medical Lead and Method of Making Same".

FIELD OF THE INVENTION

The present invention relates to medical apparatus and methods. More specifically, the present invention relates to implantable medical leads and methods of manufacturing such leads.

BACKGROUND OF THE INVENTION

Existing implantable medical leads for use with implantable pulse generators, such as neurostimulators, pacemakers, defibrillators or implantable cardioverter defibrillators ("ICD"), are prone to heating and induced current when placed in the strong magnetic (static, gradient and RF) fields of a magnetic resonance imaging ("MRI") machine. The heating and induced current are the result of the lead acting like an antenna in the magnetic fields generated during a MRI. Heating and induced current in the lead may result in deterioration of stimulation thresholds or, in the context of a cardiac lead, even increase the risk of cardiac tissue damage and perforation.

Over fifty percent of patients with an implantable pulse generator and implanted lead require, or can benefit from, a MRI in the diagnosis or treatment of a medical condition. MRI modality allows for flow visualization, characterization of vulnerable plaque, non-invasive angiography, assessment of ischemia and tissue perfusion, and a host of other applications. The diagnosis and treatment options enhanced by MRI are only going to grow over time. For example, MRI has been proposed as a visualization mechanism for lead implantation procedures.

There is a need in the art for an implantable medical lead configured for improved MRI safety. There is also a need in the art for methods of manufacturing and using such a lead.

BRIEF SUMMARY OF THE INVENTION

An implantable medical lead is disclosed herein. In one embodiment, the lead includes a body and an electrical pathway. The body may include a distal portion with an electrode and a proximal portion with a lead connector end. The electrical pathway may extend between the electrode and lead connector end and include a coiled inductor including a first portion and a second portion at least partially magnetically decoupled from the first portion. The first portion may include a first configuration having a first SRF. The second portion may include a second configuration different from the first configuration. The second configuration may have a second SRF different from the first SRF. For example, the first SRF may be near 64 MHz and the second SRF may be near 128 MHz.

An implantable medical lead is disclosed herein. In one embodiment, the lead includes a body and an electrical pathway. The body may include a distal portion with an electrode and a proximal portion with a lead connector end. The electrical pathway may extend between the electrode and lead connector end and include a coiled inductor including a coiled inductor including a magnetic shielding layer dividing the coiled inductor into a proximal region and a distal region at least partially magnetically decoupled from the proximal region. The proximal region may have a SRF that is different from a SRF of the distal region.

Also, the SRF for the proximal region and the SRF for the distal region may be selected from a variety of frequencies, such as, for example, frequencies for common MRI scans like approximately 64 MHz and approximately 128 MHz. The magnetic shielding layer may have at least one of a ring and disc configuration, and may be made of at least one of a non-magnetic metal and a polymer loaded with a non-magnetic metal.

An implantable medical lead is disclosed herein. In one embodiment, the lead includes a body, a first electrical pathway, a second electrical pathway, and a magnetic shielding layer. The body may include a distal portion and a proximal portion. The distal portion may include a tip electrode and a ring electrode proximal of the tip electrode. The proximal portion may include a lead connector end. The first electrical pathway may extend between the tip electrode and lead connector end and include a first inductor. The second electrical pathway may extend between the ring electrode and lead connector end and include a second inductor. The magnetic shielding layer may at least partially magnetically decoupling the first inductor from the second inductor.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
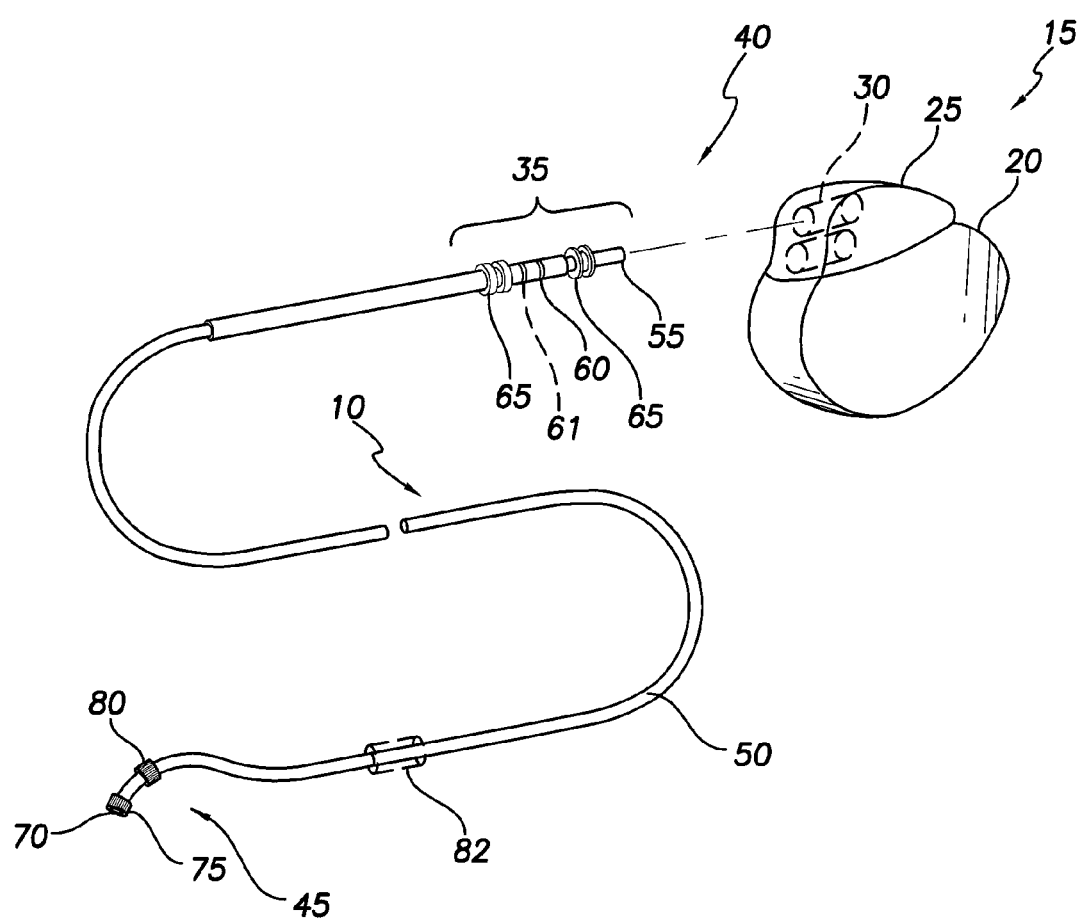
FIG. 1 is an isometric view of an implantable medical lead and a pulse generator for connection thereto.

Disclosed herein is an implantable medical lead 10 employing a lumped inductor 160 near the distal end 45 of the lead 10. In one embodiment, the lumped inductor 160 may be partitioned or divided via a magnetic shielding layer ("shield") 163 to at least partially magnetically decouple the inductor 160 into separate portions 160', 160" to provide high impedance at multiple MRI scan frequencies, for example, at both 64 MHz and 128 MHz, and, perhaps, even additional scan frequencies, each portion 160', 160" being tuned to have high impedance at a specific one of the multiple MRI scan frequencies. Thus, the lumped inductor 160 may be configured to have multiple, for example, two or more, self resonant frequencies ("SRF"). Thus, regardless of which type of MRI scan, for example, 1.5T and 3.0T, the patient undergoes, the lead 10 implanted in the patient will have high impedance, substantially reducing, if not eliminating, induced currents in the lead conductors 85, 90 and the associated heating in the electrodes 75, 80. The configuration of the lumped inductor 160 results in a small size, allowing the lumped inductor 160 to be employed in 6F or smaller leads.

In one embodiment, the lumped inductor 160 is not partitioned, but is instead configured to provide a single SRF between two desired frequencies, such as, for example, 64 MHz and 128 MHz, the lumped inductor providing sufficient impedance to adequately reduce induced currents and the associated heating.

The embodiments of the lumped inductors 160 disclosed herein may be configured to have a hermetic seal or constructed with biocompatible wires so as to not require a hermetic seal for the lead to be biocompatible.

For a general discussion of an embodiment of a lead 10 employing the lumped inductor (e.g., coil inductor) 160, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. In some embodiments, the lead may be a 6 French, model 1688T lead, as manufactured by St. Jude Medical of St. Paul, Minn. In other embodiments, the lead may be a 6 French model 1346T lead, as manufactured by St. Jude Medical of St. Paul, Minn. In other embodiments, the lead 10 may be of other sizes and models. The lead 10 may be configured for a variety of uses. For example, the lead 10 may be a RA lead, RV lead, LV Brady lead, RV Tachy lead, intrapericardial lead, etc.

As indicated in FIG. 1, the proximal end 40 may include a lead connector end 35 including a pin contact 55, a first ring contact 60, a second ring contact 61, which is optional, and sets of spaced-apart radially projecting seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIG. 1, in one embodiment, the lead distal end 45 may include a distal tip 70, a tip electrode 75 and a ring electrode 80. In some embodiments, the lead body 50 is configured to facilitate passive fixation and/or the lead distal end 45 includes features that facilitate passive fixation. In such embodiments, the tip electrode 75 may be in the form of a ring or domed cap and may form the distal tip 70 of the lead body 50.

Figure 2:
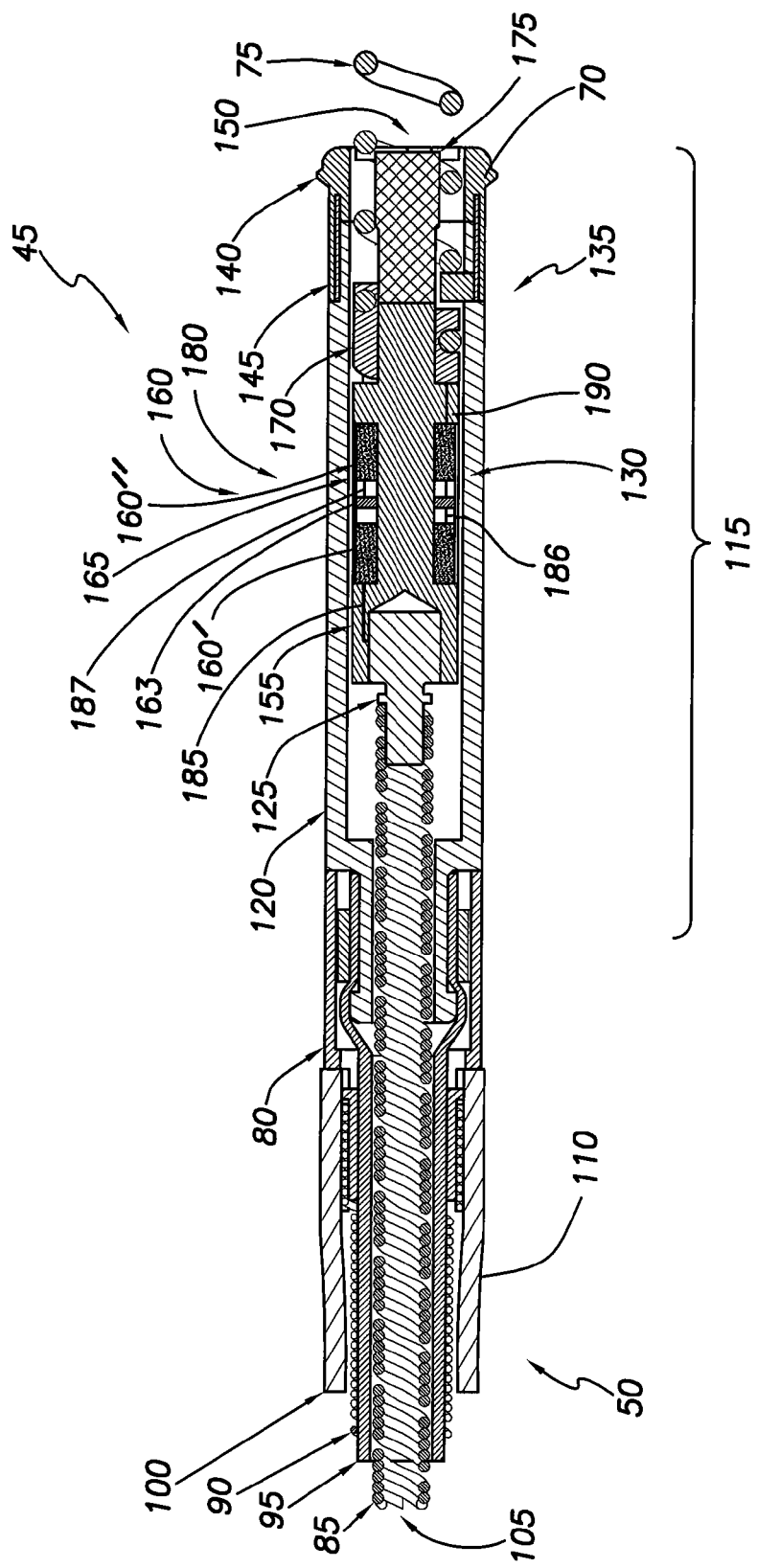
FIG. 2 is a longitudinal cross-section of the lead distal end.

As shown in FIG. 2, which is a longitudinal cross-section of the lead distal end 45, in some embodiments, the tip electrode 75 may be in the form of a helical anchor 75 that is extendable from within the distal tip 70 for active fixation and serving as a tip electrode 75.

As shown in FIG. 1, in some embodiments, the distal end 45 may include a defibrillation coil 82 about the outer circumference of the lead body 50. The defibrillation coil 82 may be located proximal of the ring electrode 70.

The ring electrode 80 may extend about the outer circumference of the lead body 50, proximal of the distal tip 70. In other embodiments, the distal end 45 may include a greater or lesser number of electrodes 75, 80 in different or similar configurations.

As can be understood from FIGS. 1 and 2, in one embodiment, the tip electrode 75 may be in electrical communication with the pin contact 55 via a first electrical conductor 85, and the ring electrode 80 may be in electrical communication with the first ring contact 60 via a second electrical conductor 90. In some embodiments, the defibrillation coil 82 may be in electrical communication with the second ring contact 61 via a third electrical conductor. In yet other embodiments, other lead components (e.g., additional ring electrodes, various types of sensors, etc.) (not shown) mounted on the lead body distal region 45 or other locations on the lead body 50 may be in electrical communication with a third ring contact (not shown) similar to the second ring contact 61 via a fourth electrical conductor (not shown). Depending on the embodiment, any one or more of the conductors 85, 90 may be a multi-strand or multi-filar cable or a single solid wire conductor run singly or grouped, for example in a pair.

As shown in FIG. 2, in one embodiment, the lead body 50 proximal of the ring electrode 80 may have a concentric layer configuration and may be formed at least in part by inner and outer helical coil conductors 85, 90, an inner tubing 95, and an outer tubing 100. The helical coil conductor 85, 90, the inner tubing 95 and the outer tubing 100 form concentric layers of the lead body 50. The inner helical coil conductor 85 forms the inner most layer of the lead body 50 and defines a central lumen 105 for receiving a stylet or guidewire therethrough. The inner helical coil conductor 85 is surrounded by the inner tubing 95 and forms the second most inner layer of the lead body 50. The outer helical coil conductor 90 surrounds the inner tubing 95 and forms the third most inner layer of the lead body 50. The outer tubing 100 surrounds the outer helical coil conductor 90 and forms the outer most layer of the lead body 50.

In one embodiment, the inner tubing 95 may be formed of an electrical insulation material such as, for example, ethylene tetrafluoroethylene ("ETFE"), polytetrafluoroethylene ("PTFE"), silicone rubber, silicone rubber polyurethane copolymer ("SPC"), or etc. The inner tubing 95 may serve to electrically isolate the inner conductor 85 from the outer conductor 90. The outer tubing 100 may be formed of a biocompatible electrical insulation material such as, for example, silicone rubber, silicone rubber-polyurethane-co-polymer ("SPC"), polyurethane, gore, or etc. The outer tubing 100 may serve as the jacket 100 of the lead body 50, defining the outer circumferential surface 110 of the lead body 50.

As illustrated in FIG. 2, in one embodiment, the lead body 50 in the vicinity of the ring electrode 80 transitions from the above-described concentric layer configuration to a header assembly 115. For example, in one embodiment, the outer tubing 100 terminates at a proximal edge of the ring electrode 80, the outer conductor 90 mechanically and electrically couples to a proximal end of the ring electrode 80, the inner tubing 95 is sandwiched between the interior of the ring electrode 80 and an exterior of a proximal end portion of a body 120 of the header assembly 115, and the inner conductor 85 extends distally past the ring electrode 80 to electrically and mechanically couple to components of the header assembly 115 as discussed below.

As depicted in FIG. 2, in one embodiment, the header assembly 115 may include the body 120, a coupler 125, an inductor assembly 130, and a helix assembly 135. The header body 120 may be a tube forming the outer circumferential surface of the header assembly 115 and enclosing the components of the assembly 115. The header body 120 may have a soft atraumatic distal tip 140 with a radiopaque marker 145 to facilitate the soft atraumatic distal tip 140 being visualized during fluoroscopy. The distal tip 140 may form the extreme distal end 70 of the lead 10 and includes a distal opening 150 through which the helical tip anchor 75 may be extended or retracted. The header body 120 may be formed of polyetheretherketone ("PEEK"), polyurethane, or etc., the soft distal tip 140 may be formed of silicone rubber, SPC, or etc., and the radiopaque marker 145 may be formed of platinum, platinum-iridium alloy, tungsten, tantalum, or etc.

As indicated in FIG. 2, in one embodiment, the inductor assembly 130 may include a bobbin 155, a coil inductor 160, a magnetic shielding layer ("shield") 163 and a shrink tube 165. The bobbin 155 may include a proximal portion that receives the coupler 125, a barrel portion about which the coil inductor 160 is wound, and a distal portion coupled to the helix assembly 135. The bobbin 155 may be formed of an electrical insulation material such as PEEK, polyurethane, or etc.

As illustrated in FIG. 2, the shrink tube 165 may extend about the coil inductor 160 to generally enclose the coil inductor 160 within the boundaries of the bobbin 155 and the shrink tube 165. The shrink tube 165 may act as a barrier between the coil inductor 160 and the inner circumferential surface of the header body 120. Also, the shrink tube 165 may be used to form at least part of a hermitic seal about the coil inductor 160. The shrink tube 165 may be formed of fluorinated ethylene propylene ("FEP"), polyester, or etc.

While a shrink 165 is depicted in FIG. 2, in some embodiments, the inductor assembly 130 may not utilize a shrink tube 165 and may not employ a hermetic seal about the coil inductor 160. For example, the coil conductor 160 may be made biocompatible by employing biocompatible drawn filled tubing ("DFT") wires for the conductors forming the coil conductor 160.

As shown in FIG. 2, a distal portion of the coupler 125 may be received in the proximal portion of the bobbin 155 such that the coupler 125 and bobbin 155 are mechanically coupled to each other. A proximal portion of the coupler 125 may be received in the lumen 105 of the inner coil conductor 85 at the extreme distal end of the inner coil conductor 85, the inner coil conductor 85 and the coupler 125 being mechanically and electrically coupled to each other. The coupler 125 may be formed of MP35N, platinum, platinum iridium alloy, stainless steel, or etc.

As indicated in FIG. 2, the helix assembly 135 may include a base 170, the helical anchor electrode 75, and a steroid plug 175. The base 170 forms the proximal portion of the assembly 135. The helical anchor electrode 75 forms the distal portion of the assembly 135. The steroid plug 175 may be located within the volume defined by the helical coils of the helical anchor electrode 75. The base 170 and the helical anchor electrode 75 are mechanically and electrically coupled together. The distal portion of the bobbin 155 may be received in the helix base 170 such that the bobbin 155 and the helix base 170 are mechanically coupled to each other. The base 170 of the helix assembly 135 may be formed of platinum, platinum-iridium alloy, MP35N, stainless steel, or etc. The helical anchor electrode 75 may be formed of platinum, platinum-iridium ally, MP35N, stainless steel, or etc.

As illustrated in FIG. 2, a distal portion of the coupler 125 may be received in the proximal portion of the bobbin 155 such that the coupler 125 and bobbin 155 are mechanically coupled to each other. A proximal portion of the coupler 125 may be received in the lumen 105 of the inner coil conductor 85 at the extreme distal end of the inner coil conductor 85 such that the inner coil conductor 85 and the coupler 125 are both mechanically and electrically coupled to each other. The coupler 125 may be formed of MP35N, stainless steel, or etc.

As can be understood from FIG. 2 and the preceding discussion, the coupler 125, inductor assembly 130, and helix assembly 135 are mechanically coupled together such that these elements 125, 130, 135 of the header assembly 115 do not displace relative to each other. Instead these elements 125, 130, 135 of the header assembly 115 are capable of displacing as a unit relative to, and within, the body 120 when a stylet or similar tool is inserted through the lumen 105 to engage the coupler 125. In other words, these elements 125, 130, 135 of the header assembly 115 form an electrode-inductor assembly 180, which can be caused to displace relative to, and within, the header assembly body 120 when a stylet engages the proximal end of the coupler 125. Specifically, the stylet is inserted into the lumen 105 to engage the coupler 125, wherein rotation of the electrode-inductor assembly 180 via the stylet in a first direction causes the electrode-inductor assembly 180 to displace distally, and rotation of the electrode-inductor assembly 180 via the stylet in a second direction causes the electrode-inductor assembly 180 to retract into the header assembly body 120. Thus, causing the electrode-inductor assembly 180 to rotate within the body 120 in a first direction causes the helical anchor electrode 75 to emanate from the tip opening 150 for screwing into tissue at the implant site. Conversely, causing the electrode-inductor assembly 180 to rotate within the body 120 in a second direction causes the helical anchor electrode 75 to retract into the tip opening 150 to unscrew the anchor 75 from the tissue at the implant site.

As already mentioned and indicated in FIG. 2, the coil inductor 160 may be wound about the barrel portion of the bobbin 155. A proximal terminal end 185 of the coil inductor 160 may extend through the proximal portion of the bobbin 155 to electrically couple with the coupler 125, and a distal terminal end 190 of the coil inductor 160 may extend through the distal portion of the bobbin 155 to electrically couple to the helix base 170. Thus, in one embodiment, the coil inductor 160 is in electrical communication with the both the inner coil conductor 85, via the coupler 125, and the helical anchor electrode 75, via the helix base 170. Therefore, the coil inductor 160 acts as an electrical pathway through the electrically insulating bobbin 155 between the coupler 125 and the helix base 170. In one embodiment, all electricity destined for the helical anchor electrode 75 from the inner coil conductor 85 passes through the coil inductor 160 such that the inner coil conductor 85 and the electrode 75 both benefit from the presence of the coil inductor 160, the coil inductor 160 acting as a lumped inductor 160 when the lead 10 is present in a magnetic field of a MRI.

As the helix base 170 may be formed of a mass of metal, the helix base 170 may serve as a relatively large heat sink for the inductor coil 160, which is physically connected to the helix base 170. Similarly, as the coupler 125 may be formed of a mass of metal, the coupler 125 may serve as a relatively large heat sink for the inductor coil 160, which is physically connected to the coupler 125.

Figure 3:
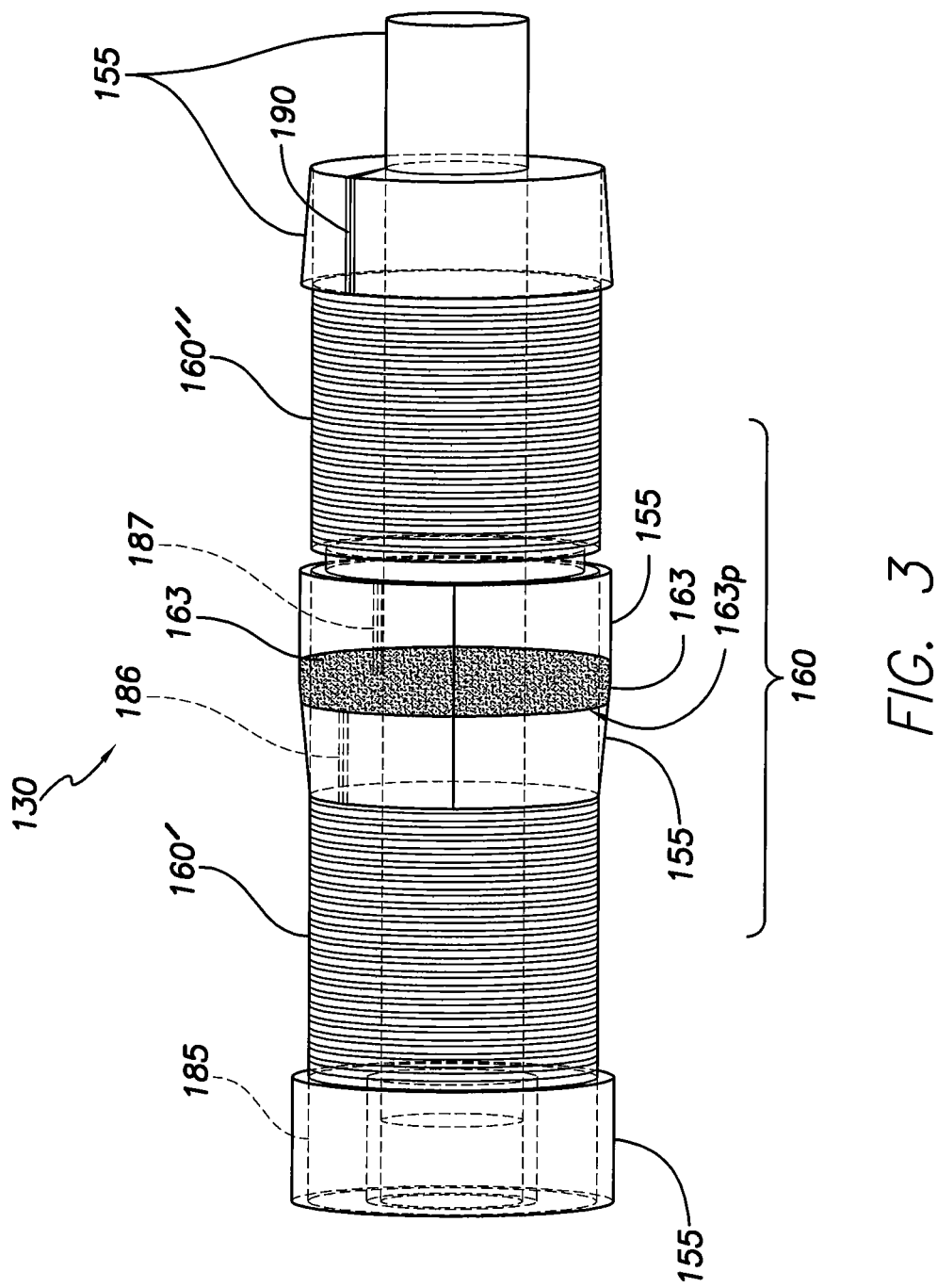
FIG. 3 is an isometric view of a coil inductor assembly having a shield separating a proximal coil inductor and a distal inductor.

As indicated in FIG. 2, the layer or shield 163 may be located within the inductor coil 160 somewhere along the length of the inductor coil 160 between the distal and proximal ends of the inductor coil 160. For example, as indicated in FIG. 3, which is an enlarged isometric view of the inductor coil assembly 130, the inductor coil 160 may be a proximal inductor coil 160' and a distal inductor coil 160" respectively wound about proximal and distal barrel portions of the bobbin 155. The shield 163 may be imbedded in the bobbin or otherwise supported in the inductor coil assembly 130 between the distal end of the proximal inductor coil 160' and the proximal end of the distal inductor coil 160". A distal end terminal 186 of the proximal inductor coil 160' may be electrically coupled to the proximal face 163p of the shield 163, and the proximal end terminal 187 of the distal inductor coil 160" may be electrically coupled to the distal face 163d of the shield 163, wherein the shield 163 is electrically conductive to complete the electrical circuit between the two inductor coils 160', 160". In other embodiments, the distal end terminal 186 of the proximal inductor coil 160' is electrically coupled to the proximal end terminal 187 of the distal inductor coil 160", and the two inductor coils 160', 160", much less the two end terminals 186, 187 are not electrically coupled to the shield 163.

As explained in greater detail below, the proximal inductor coil 160' may have a winding configuration that causes the proximal inductor coil 160' to be tuned to have a high impedance at a certain frequency, and the distal inductor coil 160" may have a winding configuration that causes the distal inductor coil 160" to be tuned to have a high impedance at another certain frequency. For example, the proximal inductor coil 160' may be tuned to have a high impedance when present in a magnetic field generated by a 1.5T MRI machine, and the distal inductor coil 160" may be tuned to have a high impedance when present in a magnetic field generated by a 3.0T MRI machine. In other words, the proximal inductor coil 160' may have a configuration to result in an appropriate self resonant frequency ("SRF") for a specific MRI frequency, such as, for example, 64 MHz for a 1.5T MRI scan, and the distal inductor coil 160" may have a configuration to result in an SRF for a specific MRI frequency, such as, for example, 128 MHz for a 3.0T MRI scan.

Due to the presence of the shield 163 between the proximal and distal inductor coils 160', 160", the two inductor coils 160', 160" are at least partially magnetically decoupled to ensure two separate SRF at, for example, 64 MHz for a 1.5T MRI machine and 128 MHz for a 3.0T MRI machine. Thus, although the inductor coil 160 of the inductor coil assembly 130 may form the only circuit extending from the inner coil conductor 85 to the tip electrode 73, the inductor coil assembly 130 may provide high impedance values for at least two different frequencies (e.g., 64 MHz and 128 MHz) or, in other words, for two different types of MRI machines (e.g., 1.5T and 3.0T). Thus, regardless of whether a patient equipped with a lead 10 having the inductor coil assembly 130 disclosed herein undergoes an MRI scan in a 1.5T or 3.0T MRI machine, the inductor coil assembly 130 will substantially reduce, if not completely eliminate, induced currents in the conductive components of the lead 10 and the associated heating.

While the embodiments of the inductor coil assembly 130 discussed herein are given in the context of being tuned to have a SRF appropriate for 64 MHz (1.5T) and 128 MHz (3.0T) MRI machines, the inductor coil assembly 130 could be tuned to have a SRF appropriate for the frequency of any other type of MRI machine currently existing or yet to be developed.

The embodiments of the inductor coil assembly 130 discussed above employ a single shield 163 to decouple two inductor coils 160', 160", each coil 160', 160" being tuned to a different frequency to allow the inductor coil assembly 130 to provide high impedance regardless of whether the patient in which the lead 10 is implanted ends up in a 1.5T or 3.0T MRI machine. However, in other embodiments, the inductor coil assembly 130 may have two, three, or more shields 163 respectively decoupling the inductor coil 160 into three, four or more coils 160', 160". Thus, such configured inductor coil assemblies 130 would be able to be tuned to three, four or more frequencies, respectively.

Figure 4:
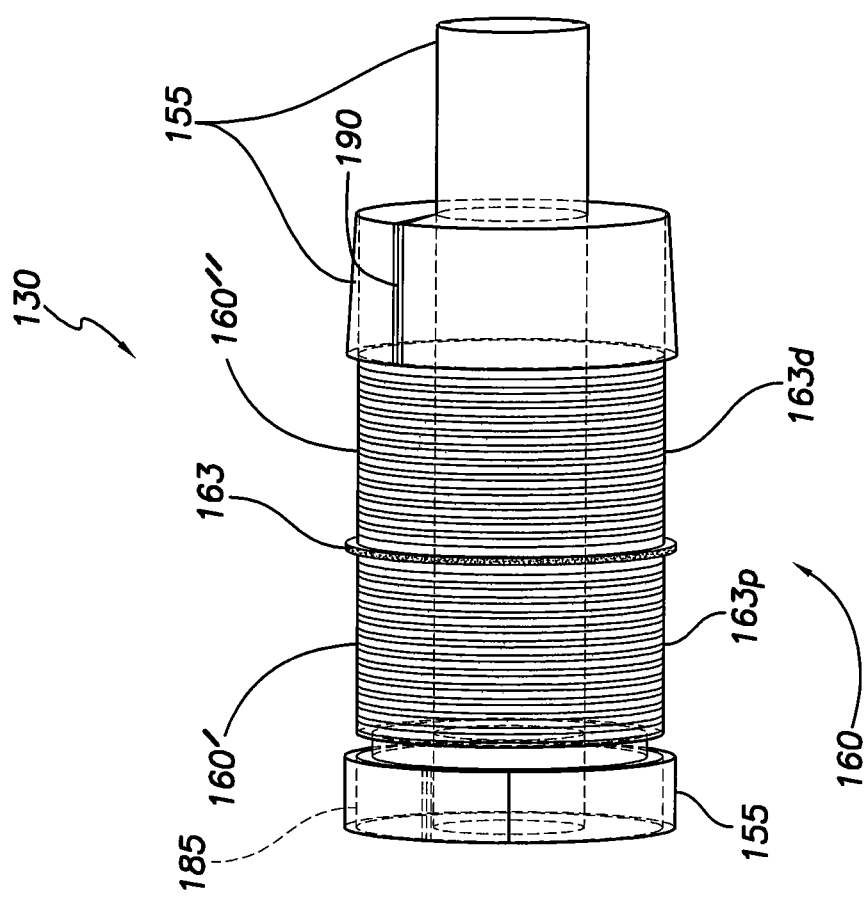
FIG. 4 is an isometric view of a coil inductor assembly having a shield that separates a coil inductor into a proximal portion and a distal portion.

As shown in FIG. 4, which is the same view as FIG. 3, except of another embodiment of the inductor assembly 130, the inductor coil 160 may actually be a single inductor coil 160 having a shield located between adjacent coils of the inductor coil 160, thereby dividing the inductor coil 160 into proximal and distal portions 160', 160". The shield 163 may or may not be electrically coupled to the inductor coil 160. For example, the proximal portion 160' of the inductor coil 160 may be wound in a configuration that results in a SRF appropriate for 64 MHz, and the distal portion 160" of the inductor coil 160 may be wound in another configuration that results in a SRF appropriate for 128 MHz. The shield 163 may be located in the inductor coil 160 in the transition windings of the inductor coil 160 where the windings of the inductor coil 160 transition from the winding configuration of the proximal portion 160' to the winding configuration of the distal portion 160". The partitioned single inductor coil 160 of FIG. 4 may then provide high impedances for two or more types of MRI machines (e.g., 1.5T and 3.0T MRI machines) in a manner similar to that of the multi-coil inductor coil 160 of FIG. 3.

In one embodiment, the shield 163 may be a flat ring having a center opening such that the shield resembles a washer in shape. In another embodiment, the shield 163 may be a flat continuous disc that is generally free of openings. In other embodiments, the shield 163 may have other shapes so long as the shield 163 is capable of decoupling the inductor coils or portions 160', 160" from each other. The shield 163 may be made of a non-magnetic (e.g., non-ferrite, etc.) metal such as, for example, Gold, Platinum (Pt), Iridium (Ir), Silver, MP35N, Titanium, or other similar non-ferrous alloy materials. Alternatively, the shield 163 may be made of an electrically conductive polymer, for example, a polymer loaded with silver, gold, platinum, etc. particles.

As indicated in FIGS. 3 and 4, the shield 163 may have a thickness Td of between approximately 2 mils and approximately 15 mils. In one embodiment the thickness Td of the shield 163 may be greater than the skin depth of magnetic flux when the inductor coil 160 is in a RF magnetic filed, such as that generated in a 1.5T or 3.0T MRI machine. In one embodiment, the thickness Td of the shield 163 may be equal to several skin depths at the highest operating frequency to be encountered by the lead 10 when the patient is being subjected to an MRI scan (e.g., 128 MHz).

In summary, the shield 163 may decouple the inductor coil 160 into a proximal inductor coil 160' and a distal inductor coil 160", as in the case of FIG. 3, or a proximal portion 160' and a distal portion 160", as in the case of FIG. 4. Decoupling the coils or portions 160', 160" by placing the shield 163 between the coils or portions 160', 160" will allow the single inductor coil assembly 130 to provide two separate SRF at two different MRI scan frequencies, for example, 64 MHz and 128 MHz.

In one embodiment, the coils or portions 160', 160" for an inductor coil 160 of an inductor coil assembly 130 designed to have high impedance at both 64 MHz and 128 MHz may be configured as follows. The proximal coil or portion 160' designed for high impedance at 64 MHz may employ 44 gauge DFT wire with an ETFE insulation layer of 0.5 mils and wound to have either five layers of 28 turns per layer or seven layers of 19 turns per layer. The distal coil or portion 160" designed for high impedance at 128 MHz may employ 44 gauge DFT wire with an ETFE insulation layer of 0.5 mils and wound to have five layers of nine to ten turns per layer. In one such embodiment, the two coils or portions 160', 160" combine to have a coil inductor length ICL of approximately 150 mils for the inductor coil 160, as indicated in FIG. 2.

Figure 5:
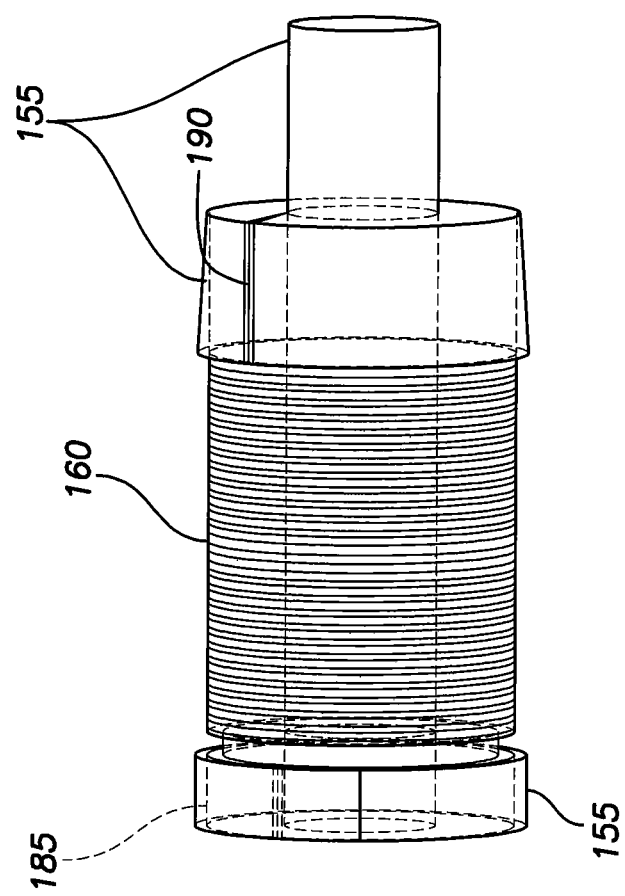
FIG. 5 is an isometric view of a coil conductor that does not employ a shield.
Figure 6:
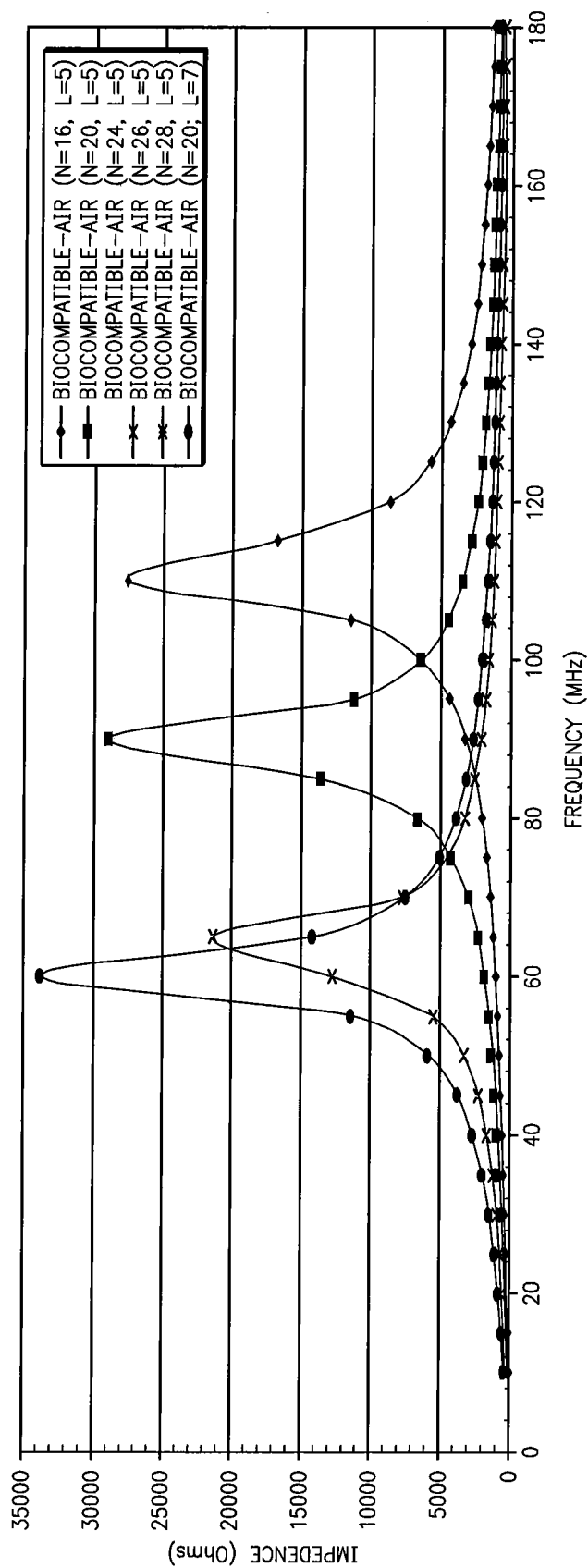
FIG. 6 is a graphical depiction of predicted SRF for different coil inductor configurations.

As indicated in FIG. 5, which is an isometric view of a inductor coil assembly 130 that does not employ a layer or shield 163, in one embodiment the inductor coil 160 may be configured to have a SRF that is generally between two expected MRI scan frequencies, such as, for example, 64 MHz and 128 MHz and yet offers sufficient impedance at these expected MRI scan frequencies. For example, as shown in FIG. 6, which is a graphical depiction of expected impedances for proposed coil configurations, a coil having five layers L and 20 turns N per layer L (N=20, L=5) may have a SRF of approximately 90 MHz, but still provide impedance at 64 MHz and 128 MHz of approximately 3000 Ohms and 2000 Ohms, respectively. Similarly, a coil having five layers L and 16 turns N per layer L (N=16, L=5) may have a SRF of approximately 116 MHz, but still provide impedance at 64 MHz and 128 MHz of approximately 1500 Ohms and 4500 Ohms, respectively.

FIG. 6 illustrates how different inductor coil configurations may be selected to find a single SRF that offers satisfactory impedance for multiple MRI scan frequencies, as discussed with respect to FIG. 5. Also, FIG. 6 illustrates how a first inductor coil configuration with a SRF that offers maximum impedance at a first MRI scan frequency (e.g., 64 MHz) and a second inductor coil configuration with a SRF that offers maximum impedance at a second MRI scan frequency (e.g., 128 MHz) may be selected for use in the inductor coil 160 of FIGS. 3 and 4.

As shown in FIG. 6, SRF shifts down from 110 MHz for an inductor coil 160 having N=16 turns and L=5 layers to 60 MHz by adding turns (N=16 up to N=28) or adding layers (L=5 or 7 with N=20). In one embodiment, an inductor coil 160 may have SRF in the vicinity of 64 MHz when configured to have L=5 layers and anywhere from approximately N=28 turns in each layer to approximately N=24 turns in each layer, the resulting length ICL being approximately 100 mils. A similar SRF can be achieved with L=7 layers with N=18 or 20 turns in each layer, the resulting length ICL being approximately 50 mils.

In order to have SRF at 128 MHz, in some embodiments, less turns are needed (e.g., N=9-10 turns; L=5 layers) with the length ICL for the coil being approximately 34 mils. Thus, FIG. 6 illustrates how a single non-partitioned coil such as that depicted in FIG. 5 may be employed to provide impedance sufficient at both 64 MHz and 128 MHz. Also, FIG. 6 illustrates how a first coil or portion 160' of a inductor coil 160 may be selected to have maximum impedance at 64 MHz while the other coil or portion 160" of the inductor coil 160 may be selected to have maximum impedance at 128 MHz, thereby making possible an inductor coil 160 that can substantially reduce induced current and associate heating regardless of the MRI scan frequency encountered by the lead 10.

In various embodiments of the coil configurations represented in FIG. 6, the inductor coil assemblies 130 employed the following materials: 44 Gauge wire (25% NP35N; 75% Ag); 0.5 mil insulation of ETFE; pitch of 3.12 mils; core radius of 2.545 mils; and bobbin (20.73 mils) of PEEK.

Figure 7:
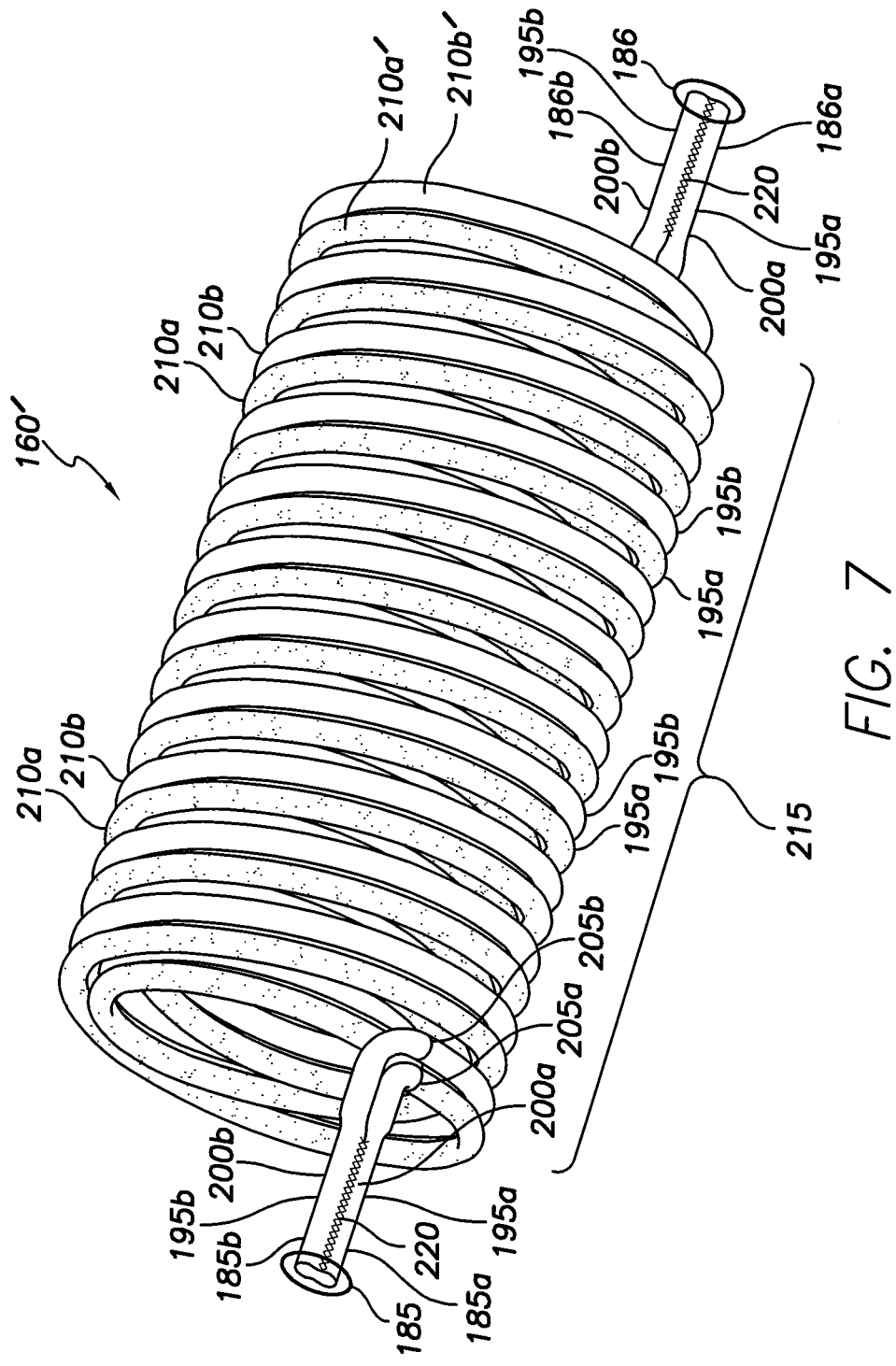
FIG. 7 is an isometric view of an inductor coil or portion of an inductor coil of an inductor coil assembly.
Figure 8:
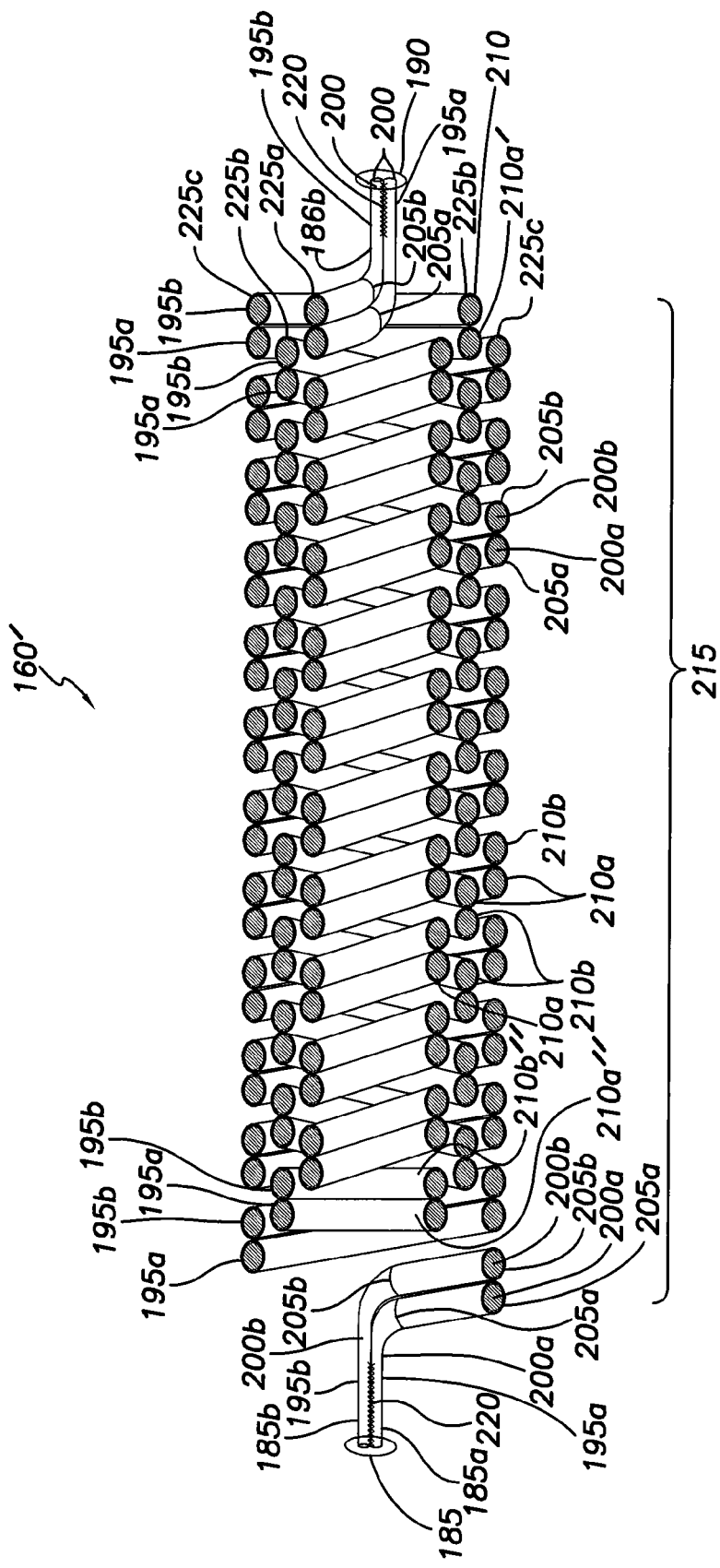
FIG. 8 is a longitudinal cross-section of the inductor coil or portion depicted in FIG. 7.

Depending on the embodiment, each helically wound coil turn of an inductor coil 160 may be a single filar, a pair of filars, a set of three filars, a set of four filars, and so on. For example, as depicted in FIGS. 7 and 8, which are, respectively, an isometric view and a longitudinal cross-section of a proximal inductor coil or portion 160' of an inductor coil 160 of an inductor coil assembly 130, each helically wound filar 195a, 195b has an electrically conductive core 200a, 200b and an electrical insulation layer 205a, 205b. Also, the coil inductor 160' may have multiple layers as discussed above, for example, three layers 225a, 225b, 225c. While this discussion takes place in the context of the proximal inductor coil 160', the teachings are equally applicable to a distal inductor coil 160" or an overall non-partitioned inductor coil 160.

As shown in FIGS. 7 and 8, the pair of helically wound filars 195a, 195b form a plurality of coils 210a, 210b, which form the coiled portion 215 of the coil inductor 160'. The coils 210a, 210b of the inner layer 225a may define a center cylindrical space that receives the barrel portion of the bobbin 155 when the coil inductor 160' is wound about the barrel portion of the bobbin 155, as indicated in FIG. 2.

As illustrated in FIGS. 7 and 8, each helically wound filar 195a, 195b terminates on the proximal end of the coil inductor 160' as proximal straight filar segments 185a, 185b, which are joined together via joining material 220, for example, a weld, solder, braze or electrically conductive epoxy, to form a unified single-piece proximal straight filar segment 185. Similarly, each helically wound filar 195a, 195b terminates on the distal end of the coil inductor 160' as distal straight filar segments 186a, 186b, which are joined together via joining material 220, for example, a weld, solder, braze or electrically conductive epoxy, to form a unified single-piece distal straight filar segment 186. The unified single-piece proximal and distal straight filar segments 185, 186 electrically couple to neighboring pieces and extend along the bobbin 155 as discussed above.

As indicated in FIGS. 7 and 8, the respective extents of the insulated filars 195a, 195b extending through the respective coils 210a, 210b of the coiled portion 215 are jacketed by respective electrical insulation layers 205a, 205b, and the respective extents of the insulated filars 195a, 195b forming the respective proximal and distal straight segments 185a, 185b, 186a, 186b may be un-insulated such that the respective electrically conductive cores 200a, 200b may be exposed. The coils 210a, 210b of the insulated filars 195a, 195b alternate with respect to position in the inductor coil 160'. The insulation layers 205a, 205b of the insulated filars 195a, 195b electrically isolate the conductor cores 200a, 200b from each other and from themselves.

As best understood from FIG. 8, the three layers 225a, 225b, 225c of the coiled inductor 160d may be wound in opposite pitch directions such that the inner and outer layers 225a, 225c are wound in a first pitch direction and the intermediate layer 225b is wound in a second opposite pitch direction. The coils 210a, 210b of the inner layer 225a are surrounded by the coils 210a, 210b of the intermediate layer 225b. The coils 210a, 210b of the intermediate layer 225b are surrounded by the coils 210a, 210b of the outer layer 225c.

The coils 210a, 210b of the outer layer 225c are wound in a first pitch direction moving distally from the proximal straight filar segments 185a, 185b until reaching the distal end of the coiled portion 215, where the coils 210a, 210b of the outer layer 225c transition into transition coils 210a', 210b' that extend into the intermediate layer 225b and have a generally neutral pitch. The coils 210a, 210b of the intermediate layer 225b are wound in a second pitch direction opposite the first pitch direction moving proximally from the transition coils 210a', 210b' until reaching the proximal end of the coiled portion 215, where the coils 210a, 210b of the intermediate layer transition into transition coils 210a", 210b" that extend into the inner layer 225a and have a generally neutral pitch. The coils 210a, 210b of the inner layer 225a are wound in the first pitch direction moving distally from the transition coils 210a", 210b" until reaching the distal end of the coiled portion 215, where the coils 210a, 210b of the inner layer 225a extend into the distal straight filar segments 186a, 186b.

The preceding discussion regarding the multi-filar multi-layer inductor coil 160' depicted in FIGS. 7 and 8 was given in the context of the multi-filar multi-layer inductor coil 160' being a bi-filar three-layer coil inductor 160'. However, in some embodiments as discussed above, the multi-filar multi-layer coil inductor 160d of FIGS. 6-7 may have three filars, four filars or more filars. Also, instead of three layers 225a, 225b, 225c, the coil inductor 160' of FIGS. 7-8 may have two layers, four layers, five layer or more layers. Even with a different number of filars and/or layers, the coiled inductor 160d of FIGS. 7-8 may have filars helically wound, alternatingly located in the helical coil, joined at their respective proximal and distal straight filar segments, and all insulated, as discussed above.

For any one or more of the coil inductor configurations discussed above with respect to FIGS. 2-8, the insulation layer 205 may be formed of polymer materials such as, for example, ETFE, PTFE, perfluoroalkoxy copolymer resin ("PFA"), polyimide, polyurethane, or etc. The insulation layer 205 may also have a radial thickness of between approximately 0.0001" and approximately 0.003".

For any one or more of the coil inductor configurations discussed above with respect to FIGS. 2-8, the conductive core 200 may be formed of an electrically conductive biocompatible material such as, for example, platinum, platinum-iridium alloy, MP35N, silver-cored MP35N, titanium, titanium alloy or etc. Alternatively, assuming adequate hermetic sealing of the coil inductor 160, the conductive core 200 may be formed of an electrically conductive non-biocompatible material such as, for example, copper or etc. The conductive core 200 may have a diameter of between approximately 0.0005" and approximately 0.005".

For any one or more of the coil inductor configurations discussed above with respect to FIGS. 2-8, the insulation 205a for the first filar 195a may be of a different material than the insulation 205b of the second filar 195b. For example, the insulation 205a for the first filar 195a may be of ETFE and the insulation 205b of the second filar 195b may be PTFE. Alternatively or additionally, the insulation 205a for the first filar 195a may be of a different thickness than the insulation 205b of the second filar 195b. For example, the insulation 205a for the first filar 195a may have a thickness of 0.001" and the insulation 205b of the second filar 195b may have a thickness of 0.002".

As can be understood from FIGS. 2-4, the inductor assembly 130 may employ two or more lumped inductors 160', 160" electrically connected in series and separated or partitioned from each other via one or more layers or shields 163. The two or more lumped inductors 160', 160" in series and separated or partitioned from each other via one or more layers or shields may each have a unique configuration that provides a unique SRF. Thus, as can be understood from FIGS. 2-4, one inductor 160' of the lumped inductors 160', 160" in series is configured to be tuned for a first frequency such as, for example, 64 MHz for 1.5T MRI scans, and the other inductor 160" of the lumped inductors 160', 160" in series is configured to be tuned for a second frequency such as, for example, 128 MHz for 3.0T MRI scans.

The decoupled inductors 160 described above with respect to FIGS. 2-8 are generally discussed in the context of being electrically coupled to a tip electrode 75. However, the concepts disclosed above with respect to the inductors 160 depicted in FIGS. 2-8 are also readily applicable to inductors 300 employed with ring electrodes 80 and other types of electrodes.

Figure 9:
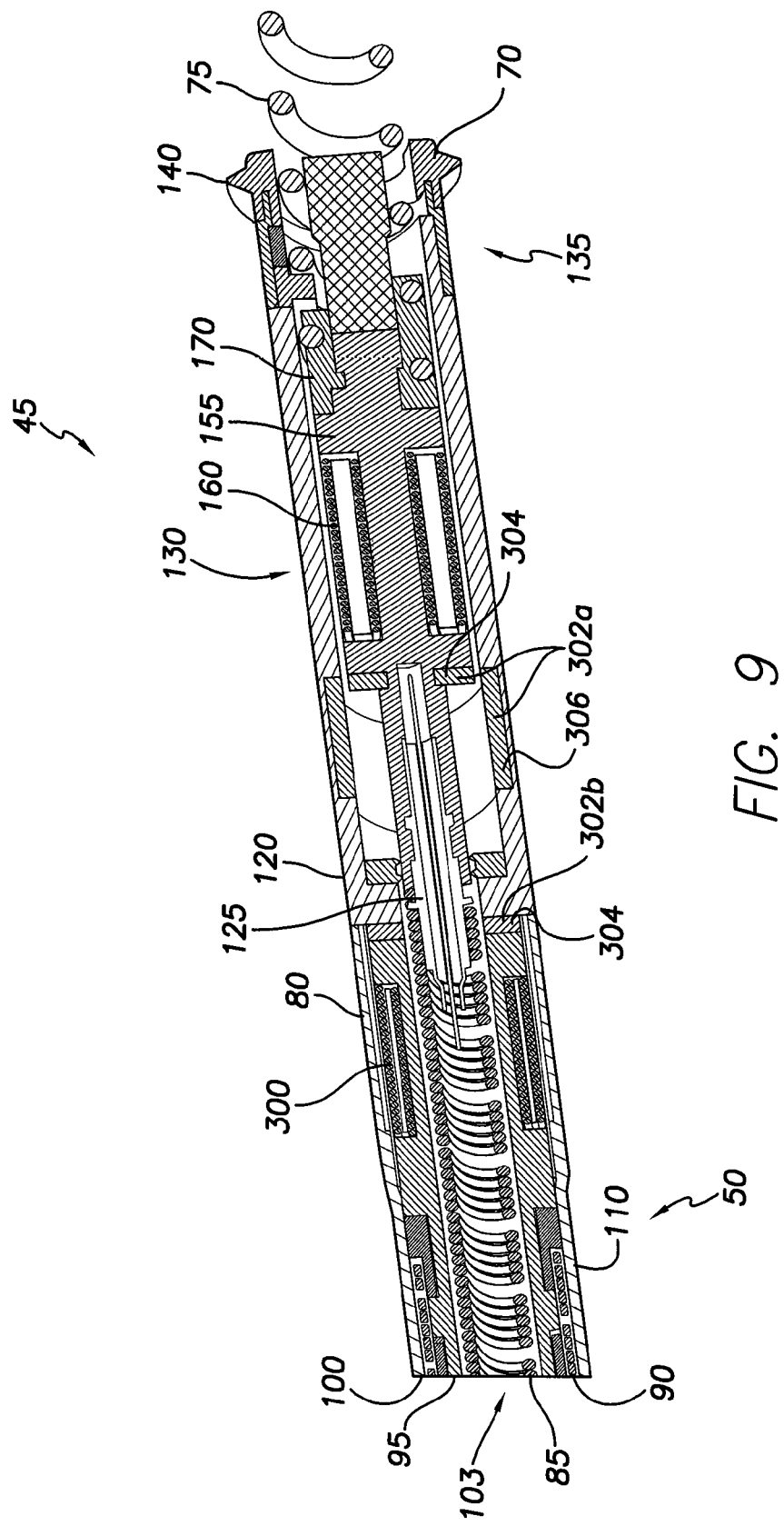
FIG. 9 is an isometric longitudinal cross section of a lead distal end of a lead having a ring inductor and a tip inductor.

Some lead embodiments may have both a tip inductor 160 and a ring inductor 300. In such embodiments, decoupling or isolating of the tip inductor 160 from the ring inductor 300 may be advantageous for many of the reasons described above. Much, if not all of the concepts discussed with respect to FIGS. 1-8 may also be applied to lead embodiments having both a ring inductor 300 and a tip inductor 160. For example, as depicted in FIG. 9, which is an isometric longitudinal cross section of a lead distal end 45, the lead 10 may have both: (1) a ring inductor 300 that is part of the electrical circuit extending between the ring electrode 80 and the outer conductor 90; and (2) a tip inductor 160 that is part of the electrical circuit between the tip electrode 75 and the inner conductor 85. In such an embodiment, one or more magnetic shielding layers ("shield") 302 may isolate or decouple the two inductors 160, 300 from each other in a manner similar to that described above. The shield 302 may be one or more layers or disks 304 that are oriented to extend transversely across a width of the lead body. Additionally, the shield 302 may include a cylindrical wall portion 306 adjacent a transversely oriented disk 304.

As with the shield 163 described above with respect to FIGS. 2-4, the shield 302 depicted in FIG. 9 may be formed of a non-magnetic, electrically conductive material. For example, the shield 302 may be formed of an electrically conductive non-ferrite metal, an electrically conductive polymer, etc.

In one embodiment where the tip inductor 160 is decoupled from the ring inductor 300, a shield 302 may be connected to the tip inductor 160 and located between the two inductors 160, 300. The shield 302 may be in the form of one or more electrically conductive, non-magnetic rings or discs 304 having an enlarged diameter and located between the two inductors 160, 300. Alternatively or additionally, the shield 302 may also be in the form of an electrically conductive, non-magnetic cylindrical layer 306 in the outer header. Such shield configurations may be formed of an electrically conductive, non-magnetic metal and/or an electrically conductive polymer material impregnated with a metal powder or flakes.

In some embodiments, the tip inductor 160 may have a SRF that is different from the SRF of the ring inductor 300. For example, one of the inductors 160, 300 may be tuned for a frequency of 64 MHz and the other of the inductors may be tuned for a frequency of 128 MHz. In such an embodiment, the two inductors 160, 300 may be magnetically decoupled from each other via one or more shields 302 located between the inductors 160, 300.

In some embodiments, the tip inductor 160 may have a SRF that is the same as the SRF of the ring inductor 300. For example, both of the inductors 160, 300 may be tuned for a frequency of 64 MHz. Alternatively, both of the inductors 160, 300 may be tuned for a frequency of 128 MHz. In such embodiments, the two inductors 160, 300 may be magnetically decoupled from each other via one or more shields 302 located between the inductors 160, 300. In other such embodiments, shields 302 may not be located between the inductors 160, 300 and the two inductors 160, 300 may not be magnetically decoupled.

Figure 10:
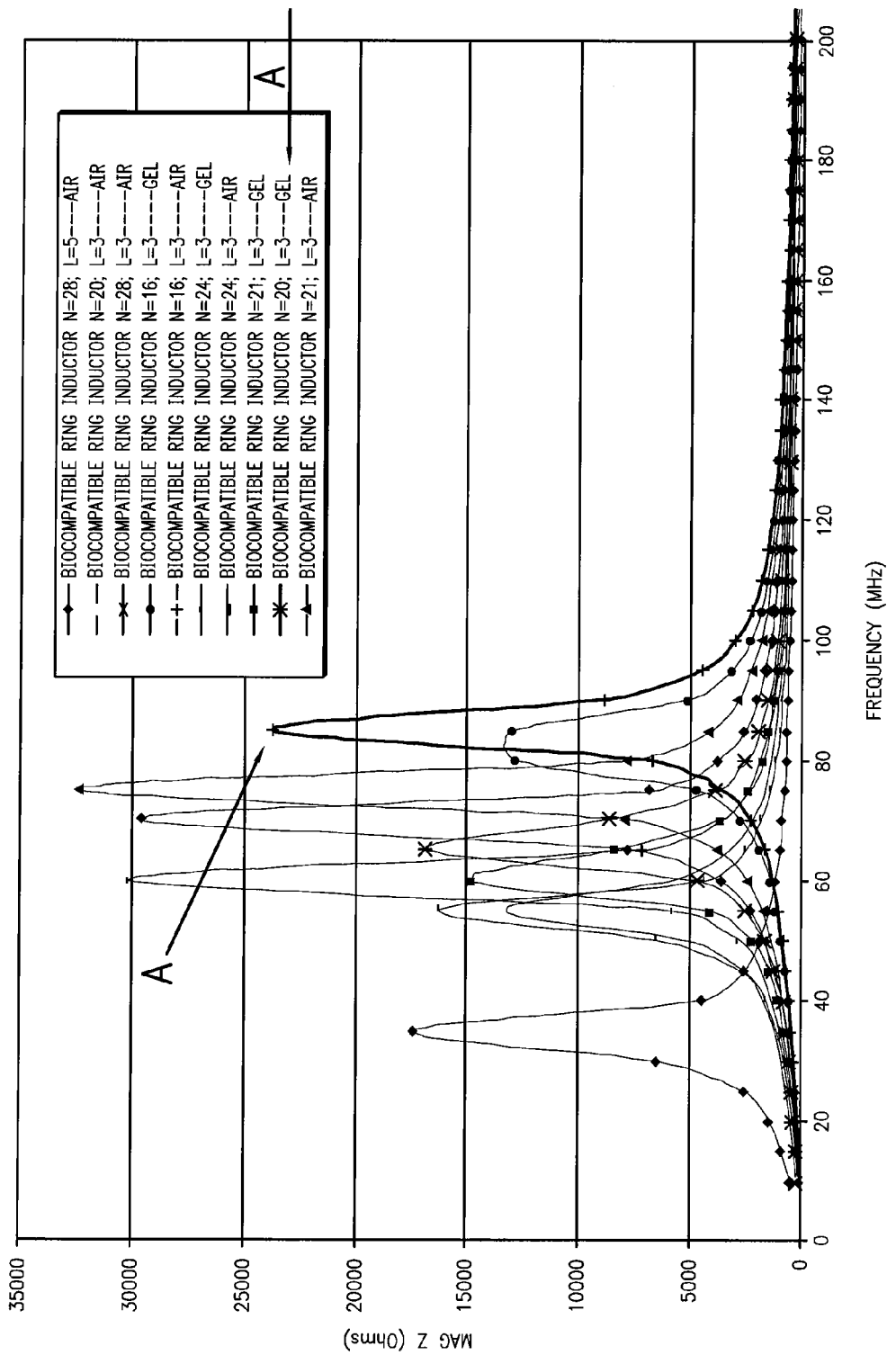
FIG. 10 illustrates how different inductor coil configurations may be selected in a manner similar to that discussed with respect to FIG. 6.

FIG. 10 illustrates how different inductor coil configurations may be selected in a manner similar to that discussed with respect to FIG. 6. As shown by arrows A in FIG. 9, a SRF of approximately 64 MHz may be obtained for an inductor coil having N=20 turns and L=3 layers. Thus, such a inductor coil configuration may substantially reduce induced current and associate heating for a lead exposed to a 1.5T MRI machine. Other coil configuration may be identified for (128 MHz) 3.0T MRI machines. Depending on the embodiment, the ring inductor 300 may have turns per layer N of between approximately 18 to approximately 60 and layers L of between approximately one and approximately three.

In various embodiments of the inductor configurations represented in FIG. 9, the inductor coil assemblies 130, 300 may employ the following materials: 42-46 Gauge DFT wire (30%-75% Ag); 0.5 mil-1.0 mil ETFE insulation. The ring inductor 300 may have a length of approximately 80 mils, an outside diameter (OD) of approximately 80 mils, and an inner diameter (ID) of approximately 55 mils. The tip inductor 160 may have a length of approximately 80 mils and an outside diameter (OD) of approximately 55 mils.

Depending on the embodiment, all portions of the shield 302 may be exclusively electrically coupled to one or the other of the two inductors 160, 300. In other embodiments, a first shield portion (e.g., shield 302a) may be exclusively electrically coupled to one of the inductors (e.g., inductor 160) and the other shield portion (e.g., 302b) may be exclusively electrically coupled to the other inductor (e.g., inductor 300). Also, in some embodiments, in addition to the inductors 160, 300 being decoupled from each other as discussed with respect to FIG. 9, one or both of the individual inductors 160, 300 may be decoupled within itself in a manner as discussed with respect to FIGS. 2-4.

While the above-discussed embodiments are generally discussed in the context of inductors being coil-type inductors, the shielding or decoupling concepts discussed herein are also applicable to inductor sets employing other types of inductors, including, for example, multi-layer inductors and integrated/printed circuit inductors. Accordingly, the shielding or inductor decoupling discussion contained herein should be interpreted to encompass all types of inductors.

Although the present invention has been described with reference to preferred embodiments, persons skilled in the art will recognize that changes may be made in form and detail without departing from the spirit and scope of the invention.

What is claimed is:

1. An implantable medical lead comprising:
a body including a distal portion with an electrode and a proximal portion with a lead connector end; and
an electrical pathway extending between the electrode and lead connector end and including a coiled inductor formed from a continuously coiled wire, the coiled inductor having a magnetic shielding layer dividing the inductor into a first portion and a second portion at least partially magnetically decoupled from the first portion, wherein the first portion of the coiled inductor includes a first configuration having a first self resonant frequency (SRF), the second portion of the coiled inductor includes a second configuration different from the first configuration, and the second configuration has a second SRF different from the first SRF.

2. The lead of claim 1, wherein the first SRF is near 64 MHz and the second SRF is near 128 MHz.

3. The lead of claim 1, wherein the the first portion includes approximately five to approximately seven layers of approximately 16 to approximately 32 turns, and the second portion includes approximately five layers of approximately five to approximately 16 turns.

4. The lead of claim 1, wherein the coiled inductor comprises a multi-filar construction.

5. The lead of claim 1, wherein the coiled inductor comprises a uni-filar construction.

6. The lead of claim 1, wherein the coiled inductor comprises filar conductors formed of a biocompatible material.

7. The lead of claim 6, wherein the biocompatible material is a drawn filled tubing (DFT) wire.

8. The lead of claim 7, wherein the drawn filled tubing (DFT) has between approximately 30% to approximately 75% silver.

9. An implantable medical lead comprising:
a body including a distal portion with an electrode and a proximal portion with a lead connector end;
an electrical pathway extending between the electrode and lead connector end and including a coiled inductor formed from a continuously coiled wire, the coiled inductor including a first portion and a second portion, wherein the second portion is at least partially magnetically decoupled from the first portion; and
a magnetic shielding layer located between the first and second portions of the coiled inductor, the layer at least partially magnetically decoupling the first and second portions from each other, wherein the layer is electrically isolated from both of the first and second portions.

10. An implantable medical lead comprising:
a body including a distal portion with an electrode and a proximal portion with a lead connector end;
an electrical pathway extending between the electrode and lead connector end and including a single continuous inductor coil formed from a continuously coiled wire, the single continuous inductor coil including a first portion and a second portion at least partially magnetically decoupled from the first portion; and
a magnetic shielding layer located between the first and second portions, the layer at least partially magnetically decoupling the first and second portions from each other, wherein the first and second portions are respectively proximal and distal portions of the single continuous inductor coil partitioned by the layer located in the single continuous inductor coil between proximal and distal ends of the single continuous inductor coil.

11. The lead of claim 10, wherein the layer has at least one of a ring-like configuration and a disc-like configuration.

12. The lead of claim 10, wherein the layer is at least one of a non-magnetic metal and a polymer including a non-magnetic metal.

13. The lead of claim 10, wherein the layer is electrically coupled to at least one of the first and second portions.

14. The lead of claim 10, wherein the first portion is electrically coupled to the second portion via the layer.

15. The lead of claim 10, wherein the single continuous inductor coil includes a transition zone between the first and second configurations and the layer is located in the transition zone.

16. The lead of claim 10, wherein the first and second portions are respectively proximal and distal individual inductor coils electrically coupled together in series, and the layer is located between a distal end of the proximal individual inductor coil and a proximal end of the distal individual inductor coil.

17. An implantable medical lead comprising:
a body including a distal portion with an electrode and a proximal portion with a lead connector end; and
an electrical pathway extending between the electrode and lead connector end and including a coiled inductor formed from a continuously coiled wire, the coiled inductor including a magnetic shielding layer dividing the coiled inductor into a proximal region and a distal region, the distal region being at least partially magnetically decoupled from the proximal region, wherein the proximal region has a SRF that is different from an SRF of the distal region.

18. The lead of claim 17, wherein the SRF for the proximal region and the SRF for the distal region are selected from the group consisting of approximately 64 MHz and approximately 128 MHz.

19. The lead of claim 17, wherein the magnetic shielding layer has at least one of a ring and disc configuration.

20. The lead of claim 17, wherein the magnetic shielding layer is formed of at least one of a non-magnetic metallic material and a polymer loaded with a non-magnetic metallic material.

* * * * *